(12) United States Patent
Barry et al.

(10) Patent No.: US 6,277,125 B1
(45) Date of Patent: Aug. 21, 2001

(54) EMBOLIC COIL DEPLOYMENT SYSTEM WITH RETAINING JAWS

(75) Inventors: David C. Barry, San Jose, CA (US); Donald K. Jones, Lauderhill, FL (US)

(73) Assignee: Cordis Neurovascular, Inc., Miami Lakes, FL (US)

( * ) Notice: Subject to any disclaimer, the term of this patent is extended or adjusted under 35 U.S.C. 154(b) by 0 days.

(21) Appl. No.: 09/399,714

(22) Filed: Sep. 21, 1999

Related U.S. Application Data

(60) Provisional application No. 60/103,090, filed on Oct. 5, 1998, and provisional application No. 60/103,224, filed on Oct. 5, 1998.

(51) Int. Cl.[7] .................................................. A61M 25/01
(52) U.S. Cl. ........................................... 606/108; 606/200
(58) Field of Search .................................. 606/108, 198, 606/200, 205–208

(56) References Cited

U.S. PATENT DOCUMENTS

| | | |
|---|---|---|
| 4,402,319 | 9/1983 | Handa et al. . |
| 5,108,407 | 4/1992 | Geremia et al. . |
| 5,122,136 | 6/1992 | Guglielmi et al. . |
| 5,217,484 | 6/1993 | Marks . |
| 5,263,964 | 11/1993 | Purdy . |
| 5,334,210 | 8/1994 | Gianturco . |
| 5,350,397 | 9/1994 | Palermo et al. . |
| 5,354,295 | 10/1994 | Guglielmi et al. . |
| 5,380,338 * | 1/1995 | Christian .............................. 606/130 |
| 5,382,259 | 1/1995 | Phelps et al. . |
| 5,423,829 | 6/1995 | Pham et al. . |
| 5,522,836 | 6/1996 | Palermo . |
| 5,540,680 | 7/1996 | Guglielmi et al. . |
| 5,578,074 | 11/1996 | Mirigian . |
| 5,601,600 | 2/1997 | Ton . |
| 5,624,449 | 4/1997 | Pham et al. . |
| 5,634,942 | 6/1997 | Chevillon et al. . |
| 5,645,564 * | 7/1997 | Northrup et al. ..................... 606/205 |
| 5,895,391 * | 4/1999 | Farnholtz ............................ 606/108 |
| 6,102,917 * | 8/2000 | Maitland et al. ..................... 606/108 |

* cited by examiner

*Primary Examiner*—Gene Mancene
*Assistant Examiner*—Michael B. Priddy
(74) *Attorney, Agent, or Firm*—Henry W. Collins

(57) ABSTRACT

An embolic coil deployment system for placing a coil at a preselected site within a vessel of the human body. The deployment system includes retaining jaws at the distal end of a catheter for holding the coil during positioning of the coil and activation means for releasing the jaws for placement of the coil at a desired position within the vessel.

11 Claims, 2 Drawing Sheets

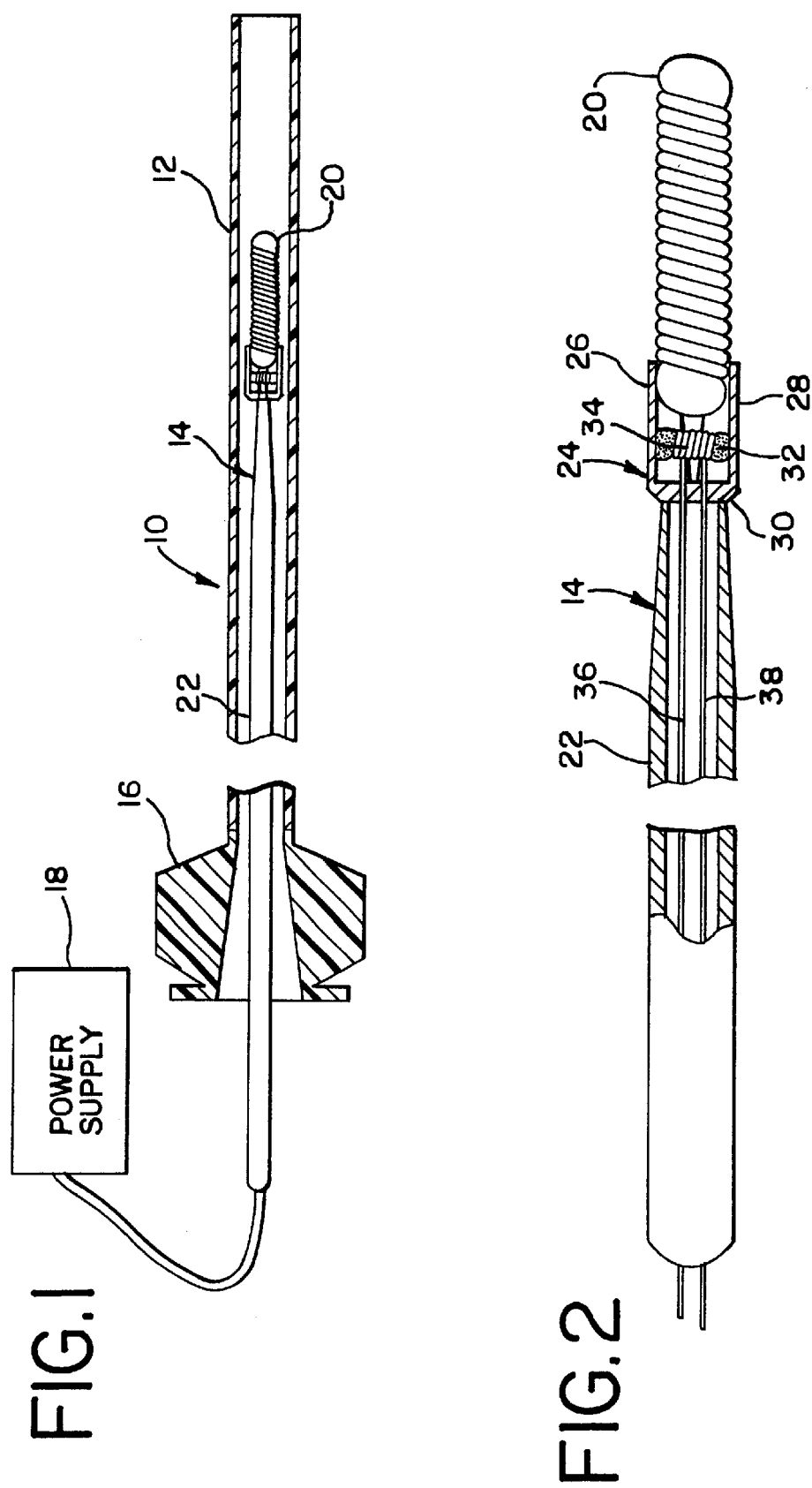

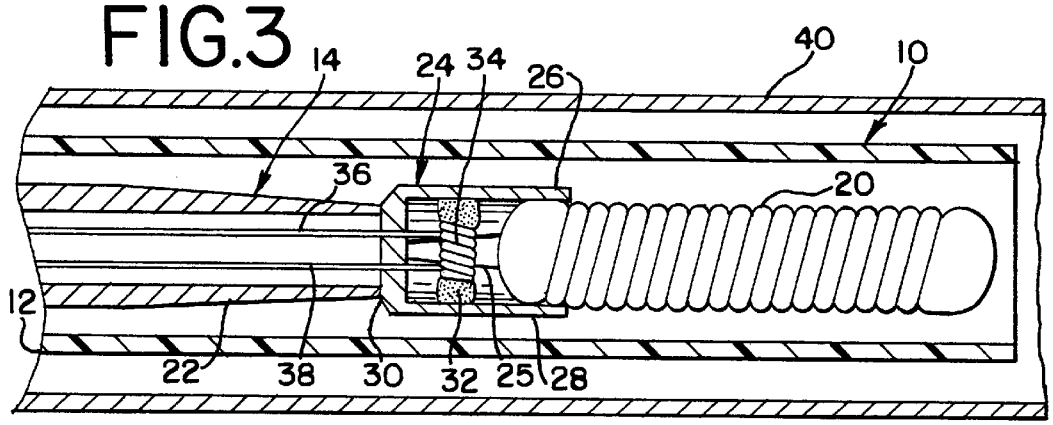
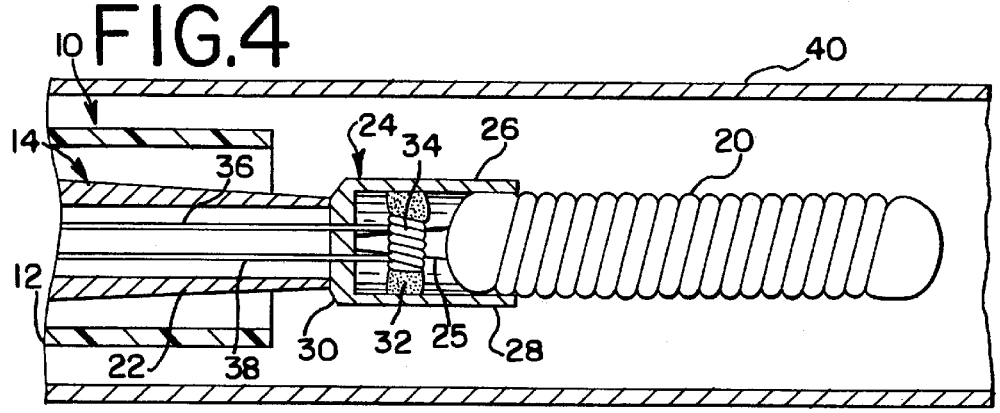
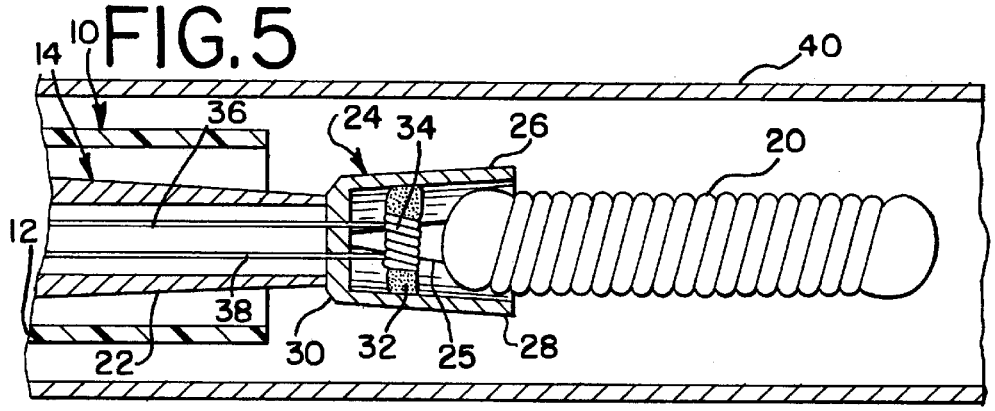
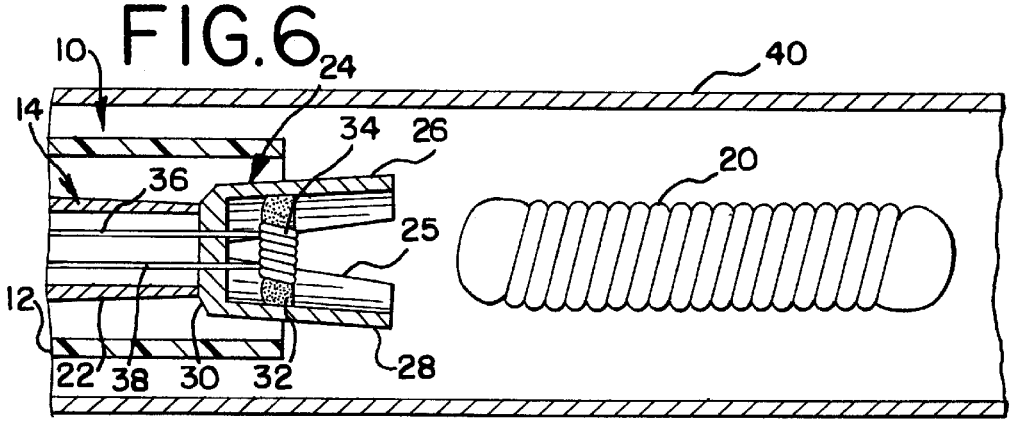

EMBOLIC COIL DEPLOYMENT SYSTEM WITH RETAINING JAWS

This application claims the benefits of Provisional No. 60/103,090 filed Oct. 5, 1998 and 60/103,224 filed Oct. 5, 1998.

BACKGROUND OF THE INVENTION

1. Field of the Invention

The present invention relates to a medical device for placing an embolic coil at a preselected location within a vessel of the human body, and more particularly, relates to a catheter having retaining jaws at the distal tip of the catheter for holding the embolic coil in order to transport the coil to a desired position within the vessel and a release mechanism for causing the jaws to open to thereby release the embolic coil at that position.

2. Description of the Prior Art

For many years flexible catheters have been used to place various devices within the vessels of the human body. Such devices include dilatation balloons, radiopaque fluids, liquid medications and various types of occlusion devices such as balloons and embolic coils. Examples of such catheter devices are disclosed in U.S. Pat. Nos. 5,108,407, entitled "Method And Apparatus For Placement Of An Embolic Coil"; 5,122,136, entitled, "Endovascular Electrolytically Detachable Guidewire Tip For The Electroformation Of Thrombus In Arteries, Veins, Aneurysms, Vascular Malformations And Arteriovenous Fistulas." These patents disclose devices for delivering embolic coils to preselected positions within vessel of the human body in order to treat aneurysms, or alternatively, to occlude the blood vessel at the particular location.

Coils which are placed in vessels may take the form of helically wound coils, or alternatively, may be random wound coils, coils wound within other coils or many other such configurations. Examples of various coil configurations are disclosed in U.S. Pat. Nos. 5,334,210, entitled, "Vascular Occlusion Assembly; 5,382,259, entitled, "Vasoocclusion Coil With Attached Tubular Woven Or Braided Fibrous Coverings." Embolic coils are generally formed of radiopaque metallic materials, such as platinum, gold, tungsten, or alloys of these metals. Often times, several coils are placed at a given location in order to occlude the flow of blood through the vessel by promoting thrombus formation at the particular location.

In the past, embolic coils have been placed within the distal end of the catheter. When the distal end of the catheter is properly positioned the coil may then be pushed out of the end of the catheter with, for example, a guidewire to release the coil at the desired location. This procedure of placement of the embolic coil is conducted under fluoroscopic visualization such that the movement of the coil through the vasculature of the body may be monitored and the coil may be placed at the desired location. With these placements systems there is very little control over the exact placement of the coil since the coil may be ejected to a position some distance beyond the end of the catheter.

Numerous procedures have been developed to enable more accurate positioning of coils within a vessel. Still another such procedure involves the use of a glue, or solder, for attaching the embolic coil to a guidewire which, is in turn, placed within a flexible catheter for positioning the coil within the vessel at a preselected position. Once the coil is at the desired position, the coil is restrained by the catheter and the guidewire is pulled from the proximal end of the catheter to thereby cause the coil to become detached from the guidewire and released from the catheter system. Such a coil positioning system is disclosed in U.S. Pat. No. 5,263,964, entitled, "Coaxial Traction Detachment Apparatus And Method."

Another coil positioning system utilizes a catheter having a socket at the distal end of the catheter for retaining a ball which is bonded to the proximal end of the coil. The ball, which is larger in diameter than the outside diameter of the coil, is placed in a socket within the lumen at the distal end of the catheter and the catheter is then moved into a vessel in order to place the coil at a desired position. Once the position is reached, a pusher wire with a piston at the end thereof is pushed distally from the proximal end of the catheter to thereby push the ball out of the socket in order to release the coil at the desired position. Such a system is disclosed in U.S. Pat. No. 5,350,397, entitled, "Axially Detachable Embolic Coil Assembly." One problem with this type of coil placement system which utilizes a pusher wire which extends through the entire length of the catheter and which is sufficiently stiff to push an attachment ball out of engagement with the socket at the distal end of the catheter is that the pusher wire inherently causes the catheter to be very stiff with the result that it is very difficult to guide the catheter through the vasculature of the body.

Another method for placing an embolic coil is that of utilizing a heat releasable adhesive bond for retaining the coil at the distal end of the catheter. One such system uses laser energy which is transmitted through a fiber optic cable in order to apply heat to the adhesive bond in order to release the coil from the end of the catheter. Such a method is disclosed in U.S. Pat. No. 5,108,407, entitled, "Method And Apparatus For Placement Of An Embolic Coil." Such a system also suffers from the problem of having a separate, relatively stiff element which extends throughout the length of the catheter with resulting stiffness of the catheter.

Still another method for placing an embolic coil is disclosed in co-pending U.S. patent application Ser. No. 09/177,848, entitled, "Embolic Coil Hydraulic Deployment System," filed on Oct. 22, 1998 and assigned to the same assignee as the present patent application. This patent application discloses the use of fluid pressure which is applied to the distal tip of the catheter for expanding the lumen of the catheter in order to release the embolic coil.

SUMMARY OF THE INVENTION

The present invention is directed toward a vascular occlusive coil deployment system for use in placing an embolic coil at a preselected site within a vessel which includes an elongated flexible positioning member having a lumen extending therethrough and having proximal and distal ends. Retaining jaws are affixed to the distal end of the positioning member. The retaining jaws have a closed position for gripping and retaining the embolic coil and an open position for releasing the coil. A heat responsive coupling member is bonded to the retaining jaws to hold the jaws in a closed position. The heat responsive coupling member exhibits the characteristic of softening and yielding upon being heated. A heating element is positioned in close proximity to the heat responsive coupling member and is adapted to be coupled to a source of energy by the use of a conductor which extends through the lumen in the delivery member. When energy is applied through the conductor to the heating element, the heating element causes the heat responsive coupling to soften and stretch to allow the retaining jaws to move to the open position to thereby release the embolic coil at the preselected site.

In accordance with another aspect of the present invention, the retaining jaws are resiliently biased toward the open position, and are preferably resiliently biased outwardly, to thereby cause the embolic coil to be released when the coupling member becomes heated.

In accordance with still another aspect of the present invention, the retaining jaws comprise two arms, which are preferably parallel to each other, which are resiliently biased outwardly. The heat responsive coupling member extends between the two arms and is bonded to the two arms for holding the jaws in a closed position.

In accordance with still another aspect of the present invention, the heating element takes the form of a resistive heating coil, and preferably the resistively heating coil is wrapped around the outer surface of the heat responsive coupling member to thereby directly apply heat to the coupling member when the coil is energized.

In accordance with still another aspect of the present invention, the energy transmission conductor takes the form of two electrical conductors which extend through the lumen of the delivery member and are connected to the resistive heating coil for applying electrical energy to the coil to thereby cause the coil to become heated.

In accordance with still a further aspect of the present invention, the heat responsive coupling member is comprised of a hot melt adhesive.

These aspects of the invention and the advantages thereof will be more clearly understood from the following description and drawings of a preferred embodiment of the present invention:

BRIEF DESCRIPTION OF THE DRAWINGS

FIG. 1 is an enlarged, partial sectional view of the vascular occlusive coil deployment system of the present invention;

FIG. 2 is an enlarged partially sectional view showing the coil deployment system prior to placement within a catheter; and, FIGS. 3 through 6 are enlarged partially sectional views illustrating the sequential steps of positioning the vascular coil within a vessel and releasing the coil at a preselected site.

DESCRIPTION OF A PREFERRED EMBODIMENT

FIG. 1 generally illustrates a preferred embodiment of a vascular occlusive coil deployment system 10 of the present invention which is comprised of an elongated flexible catheter 12 which is utilized to position a coil deployment mechanism 14. A Luer connector 16 is connected to the proximal end of the catheter 12 and the coil deployment mechanism 14 is connected to a power supply 18 for applying energy to the coil deployment mechanism 14.

FIG. 2 illustrates in more detail the construction of the coil deployment mechanism 14. More particularly, the deployment mechanism 14 includes an elongated tubular member 22 which is approximately the same length as the outer catheter 12 and which is slidably received by the catheter 12. The distal end of the tubular member 22 supports retaining jaws 24. The jaws 24 take the form of two parallel arms 26, 28 which extends from a mounting plate 30. As illustrated, the mounting plate 30 is fixedly attached to the distal tip of the tubular member 22. The parallel arms 26, 28 when in a closed position frictionally engage and tightly hold the embolic coil 20. The arms 26, 28 are held in the closed position by a heat softening adhesive 32 which extends between and is bonded to the parallel arms 26, 28.

As described, the parallel arms 26, 28 are normally biased outwardly so as to release the embolic coil 20, however, the heat softening adhesive 32 serves to hold the parallel arms in a closed position (as illustrated in FIG. 2) to thereby frictionally engage and hold the proximal section of the embolic coil 20. In the manufacture of the retaining jaws 24, the jaws preferably take the form of a cup formed from nitinol with a slot or notch 25 cut in opposing sidewalls from the opening of the cup to the bottom wall of the cup. The opposing wall, or arms 26, 28 are then bowed outwardly to the extent as shown in FIG. 5 and the retaining jaws 24, are heat set at approximately 425 degrees centigrade for 30 minutes so as to form the retaining jaws 24 in a configuration similar to that shown in FIG. 5. The arms 26, 28, which are resilient and are outwardly biased, are then pressured inwardly to tightly engage the embolic coil 20 and the heat softening adhesive 32 is heated and inserted between the arms 26, 28. When the adhesive 32 cools it serves to hold the arms 26, 27 in the closed position as shown in FIG. 3.

The heat sealing adhesive 32 may take the form of any biocompatible adhesive which, upon being heated, softens so that it may be stretched. Preferably, this heat softening adhesive is comprised of a hot melt adhesive, such as, for example, a hot melt adhesive manufactured by Minnesota Mining and Manufacturing sold under the name Jet Melt, Catalog No. 3783-TC. The temperature required to soften this material is on the order of 63 degrees centigrade.

Also, as illustrated in FIG. 2, a resistive heating element or coil 34, is wrapped around the heat softening adhesive 32 and is electrically coupled through a pair of conductors 36, 38 to the power supply 18. Accordingly, upon application of electrical current to the pair of conductors 36, 38, the resistive heating element 34 begins to heat to thereby cause the heat softening adhesive 32 to increase in temperature. As the adhesive 32 becomes warm it softens and the adhesive 32 softens and is permitted to stretch with the result that the outwardly biased arms 26, 28 move outwardly to release the embolic coil 20.

More particularly, and as illustrated in FIGS. 3 through 6, the vascular occlusive coil deployment system 10 is inserted into a blood vessel 40 and is moved to a position within the blood vessel 40 to a position where it is desirable to place the embolic coil 20. When the catheter 12 has been positioned at a location slightly proximal of the preselected site for placement of the embolic coil (FIG. 4), the coil deployment mechanism 14 is pushed out of the distal end of the catheter 12 and electrical energy is then applied to the resistive heating coil 34 to thereby soften the adhesive 32. Once the adhesive softens, the outwardly biased parallel arms 26, 28 move from a closed position (FIG. 4)to an outwardly biased open position (FIG. 5). As the parallel arms open, there is no longer engagement between the parallel arms and the embolic coil 20 and the coil is released from the retaining jaws.

Finally, and as illustrated in FIG. 6, the coil deployment mechanism 14 is withdrawn back into the catheter 12 and the embolic coil 20 remains in its deployed position.

With the vascular occlusive coil deployment system of the present invention it is possible to place an embolic coil very precisely at a desired location within a vessel. Once the coil has been placed in a preselected location by catheter, the deployment mechanism may be activated by applying energy to a coil release mechanism to thereby cause the coil to be released and deposited at a desired location.

As is apparent, there are numerous modifications of the preferred embodiment described above which will become readily apparent to one skilled in the art, such as many variations and modifications of the deployment system including many different variations of the retaining jaws, many variations of energy sources for heating the adhesive, and many variations of heat softening adhesives.

These modifications would be apparent to those having ordinary skill in the art to which this invention relates and are intended to be within the scope of the claims which follow.

That which is claimed is:

1. A vasoocclusive coil deployment system for use in placing a coil at a preselected site within a vessel comprising:
   an elongated flexible positioning member having a lumen extending therethrough and having proximal and distal ends;
   an embolic coil;
   retaining jaws affixed to the distal end of the positioning member, said jaws having a closed position for gripping and retaining said embolic coil and an open position for releasing said embolic coil, and said jaws being resiliently biased to the open position;
   an energy transmission conductor extending through the lumen of the positioning member and extending from the proximal end to the distal end of the positioning member;
   a heat responsive coupling member bonded to said retaining jaws to hold the jaws in the closed position, said heat responsive coupling member exhibits the characteristic of, upon being heated, softening thereby decreasing its tensile strength; and,
   a heating element mounted in close proximity to the beat responsive coupling member and being coupled to the energy transmission conductor whereby upon applying energy through the energy transmission conductor to the heating element, the heating element causes the heat responsive coupling member to soften and yield thereby causing the retaining jaws to move from the normally closed position to the open position to release the embolic coil at the preselected site.

2. A vasooclusive coil deployment system as defined in claim 1, wherein the heating element comprises a resistive heating coil.

3. A vasooclusive coil deployment system as defined in claim 2, wherein the resistive heating coil is wrapped around an outer surface of the heat responsive coupling member.

4. A vasoocclusive coil deployment system for use in placing a coil at a preselected site within a vessel comprising:
   an elongated flexible positioning member having a lumen extending therethrough and having proximal and distal ends;
   an embolic coil;
   retaining jaws affixed to the distal end of the positioning member, said jaws having a closed position for gripping and retaining said embolic coil and an open position for releasing said embolic coil, and said jaws being resiliently biased to the open position;
   an energy transmission conductor extending through the lumen of the positioning member and extending from the proximal end of the positioning member to the distal end of the positioning member;
   a heat responsive adhesive member bonded to said retaining jaws to hold the jaws in the closed position, said heat responsive adhesive member exhibits the characteristic, upon being heated, of softening;
   a heating element mounted in close proximity to the heat responsive adhesive member and being coupled to the energy transmission conductor whereby upon applying energy through the energy transmission conductor to the heating element, the heating element causes the heat responsive adhesive member to soften and yield thereby causing the retaining jaws to move from the normally closed position to the open position to release the embolic coil at the preselected site.

5. A vasooclusive coil deployment system as defined in claim 4, wherein the retaining jaws are resiliently biased outwardly.

6. A vasooclusive coil deployment system as defined in claim 5, wherein the retaining jaws comprise two arms which are resiliently biased outwardly and the heat responsive adhesive member extends between the two arms and is bonded to the two arms for holding the jaws in the closed position.

7. A vasooclusive coil deployment system as defined in claim 4, wherein the heating element comprises a resistive heating coil.

8. A vasooclusive coil deployment system as defined in claim 7, wherein the resistive heating coil is wrapped around an outer surface of the heat responsive adhesive member.

9. A device deployment system for use in placing a device at a preselected site within a vessel comprising:
   an elongated flexible positioning member having a lumen extending therethrough and having proximal and distal ends;
   retaining jaws affixed to the distal end of the positioning member, said jaws having a closed position for gripping and retaining a device and an open position for releasing the device, and said jaws being resiliently biased to the open position;
   an energy transmission conductor extending through the lumen of the positioning member and extending from the proximal end of the positioning member to the distal end of the positioning member;
   a heat responsive adhesive member bonded to said retaining jaws to hold the jaws in the closed position, said heat responsive adhesive member exhibits the characteristic, upon being heated, of softening;
   a heating element mounted in close proximity to the heat responsive adhesive member and being coupled to the energy transmission conductor whereby upon applying energy through the energy transmission conductor to the heating element, the heating element causes the heat responsive adhesive member to soften and yield thereby causing the retaining jaws to move from the normally closed position to the open position to release the device at a preselected site.

10. A device deployment system as defined in claim 9, wherein the heating element comprises a resistive heating coil.

11. A device deployment system as defined in claim 10, wherein the resistive heating coil is wrapped around an outer surface of the heat responsive adhesive member.

* * * * *

UNITED STATES PATENT AND TRADEMARK OFFICE
CERTIFICATE OF CORRECTION

PATENT NO. : 6,277,125 B1
DATED : August 21, 2001
INVENTOR(S) : Barry et al.

It is certified that error appears in the above-identified patent and that said Letters Patent is hereby corrected as shown below:

Column 5,
Line 19, after the word member, please insert: -- wherein the retaining jaws comprise two arms which are resiliently biased outwardly, --
Line 29, after the word jaws, please insert: -- wherein said heat responsive coupling member extends between the two arms and is bonded to the two arms for holding --
Line 29, delete the words "to hold"

Column 6,
Line 35, after the word member, please insert: -- wherein the retaining jaws comprise two arms which are resiliently biased outwardly, --
Line 36, after the word retaining, please insert -- The --
Line 36, delete the word "a"
Line 45, after the word jaws, please insert: -- , wherein said heat responsive adhesive member extends between the two arms and is bonded to the two arms for holding --
Line 45, delete the words "to hold"

Signed and Sealed this

Twenty-third Day of April, 2002

Attest:

Attesting Officer

JAMES E. ROGAN
Director of the United States Patent and Trademark Office